United States Patent [19]
Arneson et al.

[11] 3,939,824
[45] Feb. 24, 1976

[54] PHYSIOLOGICAL WAVEFORM DETECTOR
[75] Inventors: Harold N. Arneson, Oak Creek; Louis J. Heitlinger, Waukesha, both of Wis.
[73] Assignee: General Electric Company, Schenectady, N.Y.
[22] Filed: Jan. 9, 1975
[21] Appl. No.: 539,698

Related U.S. Application Data
[62] Division of Ser. No. 404,408, Oct. 9, 1973, Pat. No. 3,878,833.

[52] U.S. Cl. .................... 128/2.05 A; 128/2.06 A
[51] Int. Cl.² .......................................... A61B 5/04
[58] Field of Search...... 128/2.06 A, 2.06 B, 2.06 F, 128/2.06 G, 2.05 A, 2.05 M, 2.05 P, 2.05 Q, 2.05 R, 2.05 T

[56] References Cited
UNITED STATES PATENTS
3,524,442  8/1970  Horth.......................... 128/20.6 A
3,606,882  9/1971  Abe et al. ..................... 128/2.05 A
3,861,387  1/1975  Lawhorn et al................ 128/2.06 A Primary Examiner—William E. Kamm
Attorney, Agent, or Firm—Ralph G. Hohenfeldt; Fred Wiviott

[57] ABSTRACT

A physiological waveform detector such as for cardiac R-wave and blood pressure uses a comparator to compare the derivative of the waveform signal with a reference signal representing some percentage of the magnitude of the derivative of the waveform. If the derivative is of sufficient magnitude to trip the comparator a timing circuit begins counting. If the comparator remains tripped for a predetermined interval, the waveform is considered to be the desired one. Means are provided for detecting waveform peaks and valleys. The detector recognizes desired waveforms by two characteristics, one being magnitude and the other being duration.

7 Claims, 11 Drawing Figures

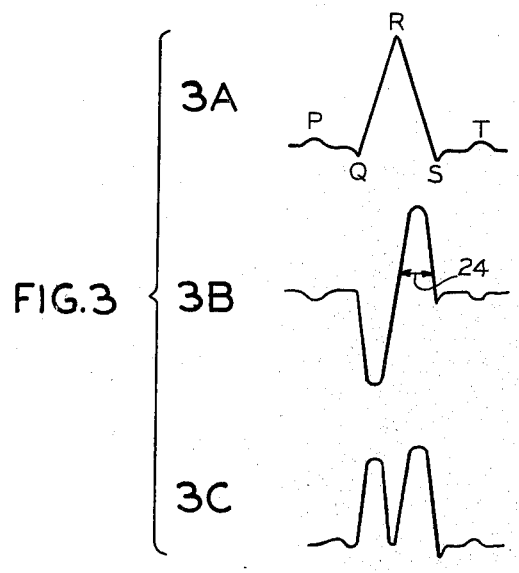
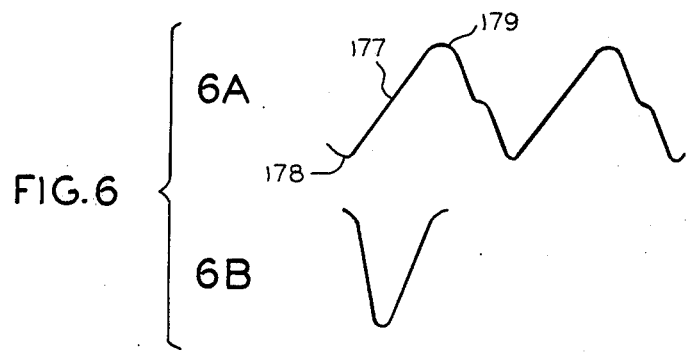

PHYSIOLOGICAL WAVEFORM DETECTOR

This is a division of application Ser. No. 404,408, filed Oct. 9, 1973, now U.S. Pat. No. 3,878,833.

BACKGROUND OF THE INVENTION

This invention relates to a device for detecting electric waveforms which are functionally related to physiological characteristics such as the electrocardiograph (ECG), blood pressure and respiration of a patient. Two uses of the invention will be illustrated and described, the first being for detecting the R-wave or QRS complex of the ECG and the second being for detecting systolic and diastolic blood pressure.

R-wave detectors used in the past generally fall into two classes. The first employs a notch filter and is based on the principle that the QRS complex is rich in 10 to 17 Hz frequency components and that the ECG waveform can be passed through a filter which has a center frequency of about 10 Hz so that the accentuated frequency can be detected. A problem with this class of detectors is that the T-wave of the ECG signal and other bioelectric muscle noise often present in the waveforms of critically ill patients contain components with about the same frequency range so it is difficult for the detector to distinguish them from a true R-wave or QRS complex. Moreover, the QRS portion of the ECG waveform with certain types of heart defects is much wider than the normal or average width for a healthy subject so it is also rich in frequencies lower than the center frequency of the filter which is set for the normal QRS complex. In addition, the peak-to-peak amplitude of a QRS complex can vary between patients and within a single patient by a factor of 25 to 1 which precludes use of an effective automatic gain control since such control usually cannot cover this wide variation and still be linear.

Another class of R-wave detectors operates on the principle that the slope of the leading and trailing edges of the QRS complex are uniquely different from those of the P and T wave portions of the ECG. The assumption is, therefore, that the derivative of the ECG waveform can be obtained and that when the output exceeds some preset threshold value, the equivalent of some preset slope, that this can be detected. The disadvantage of prior derivative class detectors is that some technique must be used to limit the slew rate of the amplifier prior to the detector circuit or muscle spikes and artificial electronic pacemaker pulses which are often present will have slopes equal to or greater than that of the QRS complex. Such similar slopes are hard to distinguish from the R-wave slopes. This class of detectors also cannot be compensated effectively with automatic gain control since the amplitude variation range is very great and the control will not respond in a linear fashion throughout a wide enough range.

Detection of other physiological waveforms or signals present similar problems. The blood pressure signal is an example. The rising edge of this waveform has a characteristic slope which is used to detect the arterial blood pressure signal. When the upslope is detected, the past minimum point is sampled and called the diastolic pressure and the following peak is sampled and called the systolic pressure. In detection of systolic upslope with presently available equipment, an integration of the original pressure waveform is compared with the unintegrated waveform to detect the arterial blood pressure signal. When the upslope is detected, the diastolic and systolic points are sampled. Since the peak and valley detection is done with diodes in an open loop scheme, the voltage drop produced by these diodes must be compensated for in the sample and hold circuit, thus requiring an adjustment. Two basic disadvantages of this class of detectors are: 1) the detection of the upslope is such that low pulse pressures such as pulmonary arterial pressure are missed, thus leaving the peak and valley detection to automatically update; and 2) since the diode drops are evident in the systolic and diastolic detectors, a change in slope will cause a different diode drop, thus changing the peak voltage detected.

Another technique for detection of the systolic and diastolic pressure is to discharge two capacitors used for peak detection alternately such that one or the other capacitor maintains the peak voltage of the systolic pressure at all times. The same technique is used for valley detection. No systolic upslope detector is used. This approach has the following disadvantaes: 1) without the use of the systolic upslope detector, accurate measurement of the systolic and diastolic points are hard to obtain; 2) if a noise spike causes one of the two capacitors to charge to an erroneous level, it will be held until that capacitor is discharged which could take as long as 5 seconds; and 3) with the loss of a signal, it may take as long as one complete discharge cycle to identify the problem and this could take 5 seconds.

SUMMARY OF THE INVENTION

In general terms, the new physiological waveform detector is characterized by using two criteria of the waveform; namely, magnitude and time to affirm that the waveform desired to be detected exists. The detector operates on the principles that the slopes of a QRS complex and a blood pressure waveform as examples, are unique as compared with other portions of the waveforms and other low frequency artifacts or noise and that the time during which the magnitude is maintained is uniquely different from that of muscle spikes, pacemaker pulses and other high frequency artifacts which may be sensed in the patient's body. The invention is further characterized by recognizing that the magnitude of the derivative, which is the first criteria for detecting a waveform, is itself directly proportional to the actual slope of the individual patient's QRS complex and, therefore, varies from patient to patient. The device further depends on establishing the optimum value for the time duration of the waveform portion in question and, as indicated above, this is used as the second criteria for detecting the wave characteristics. The reference threshold value is also varied by way of a closed loop circuit to compensate for variations in the slope of the waveforms from patient to patient.

Accordingly, a general object of this invention is to increase the reliability of detecting physiological waveforms obtained from patients even though the waveform may be suppressed or distorted as is often the case in critically ill patients.

A further object is to provide a physiological waveform detector which rejects noise such as muscle spikes, electronic pacemaker pulses or other artifacts which are common in the waveforms of critically ill patients and even in reasonably healthy patients.

Yet another object is to automatically compensate for slope variations in waveforms obtained from different patients or from a given patient over a period of time.

Another object is to reduce the number of instances in which sensitivity adjustments must be made in order to obtain reliable physiological information.

Other objects are to provide for accurately identifying peaks and valleys in waveforms and to reject artifacts whose slopes are greater or less than the upslope of the waveform portion under examination.

A further general object of this invention is to provide a detection circuit for a variety of physiological waveforms which are characterized by having unique up and down slopes.

How the foregoing and other more specific objects of the invention are achieved will appear in the detailed description of illustrative embodiments of the invention which will be set forth in reference to the drawings.

DESCRIPTION OF THE DRAWINGS

FIG. 3 depicts some waveforms which are useful for explaining the R-wave detector;

FIG. 6 shows some waveforms that are useful in explaining the invention.

DESCRIPTION OF A PREFERRED EMBODIMENT

A general description of a device for detecting the QRS or R-wave in the ECG of a patient will first be described in reference to the FIG. 1 block diagram of this type of detector. As is well known, the presence of an R-wave is indicative of the ventricles of the heart being stimulated by a natural heart signal to contract.

Figure 1:
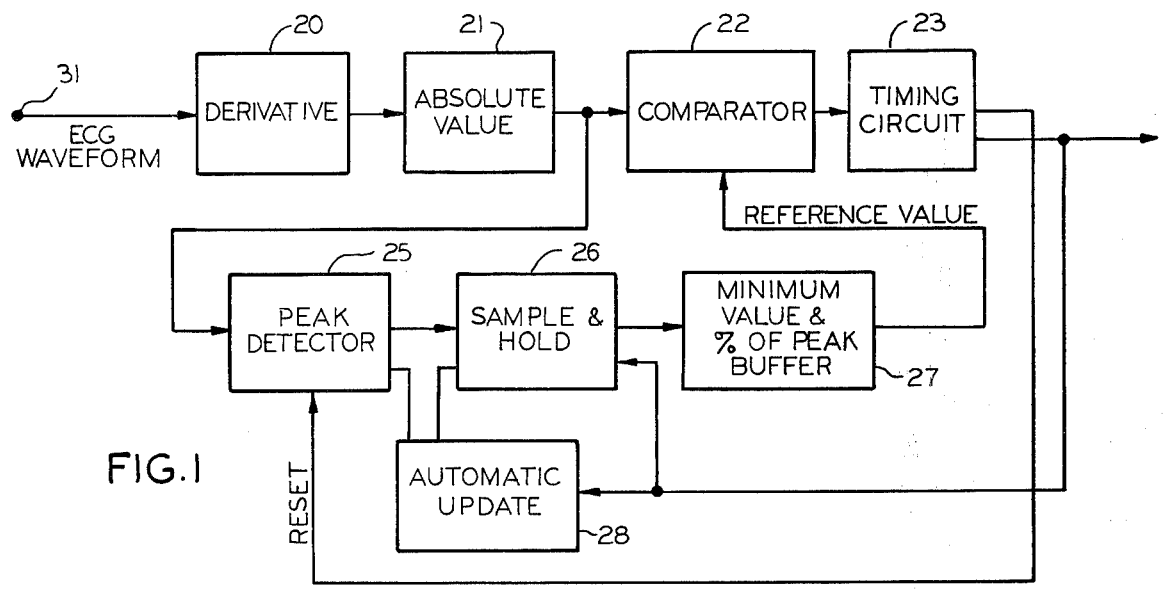
FIG. 1 is a block diagram of a device for detecting the R-wave or QRS complex of an ECG waveform.

In FIG. 1, the ECG waveform having a configuration similar to that which appears in part 3A of FIG. 3 is applied to input terminal 31 and is fed into a derivative stage 20 wherein the first derivative of the incoming ECG waveform such as that shown in part 3B of FIG. 3 is obtained. Since the slope of the QRS complex can be either positive or negative, the derivative of the leading edge can be either positive or negative. Accordingly, the derivative is processed in an absolute value circuit 21 which converts all portions of the derivative output signal to one polarity such as positive polarity as indicated by the curve in part 3C of FIG. 3.

A comparator 22 is used to compare the absolute value signal against a reference amplitude to determine if the input ECG signal or other signal present meets the derivative magnitude criteria of a QRS complex. If so, the signal is possibly an R-wave. As soon as the derivative of the ECG waveform trips the comparator, a timing circuit 23 begins counting. If the comparator 22 remains tripped for a selected time interval, then the possible candidate is accepted as a QRS complex. In this example, the timing circuit 23 produces output pulses at about 11 milliseconds, about 125 milliseconds and about 203 milliseconds. The production of a pulse at about 11 milliseconds is based upon the fact that the minimum time of the derivative of the R-wave upslope and/or downslope is substantially 11 milliseconds or greater as indicated by the dimension line 24 on the derivative curve, part B of FIG. 3. One may see that the derivative circuit 20 is designed so that the derivative of the upslope or QR segment of the QRS complex is a straight line or constant as is the derivative of the uniform downslope or RS segment. This 11 millisecond time interval 24 is the time criteria mentioned earlier as being used in conjunction with magnitude to verify existence of an R-wave. If the comparator 22 falls back to zero before the 11 millisecond time is up, such as it might do if it had switched due to a noise pulse of shorter duration, the counters in the timing circuit 23 clear and are made ready to test a new candidate waveform after having rejected the last one for failing to meet the time criteria even though it may have met the magnitude criteria.

In the FIG. 1 system, the most positive peak of the derivative waveform absolute value such as in part C of FIG. 3, is detected or monitored in a peak detector 25. The amplitude of the reference value, in terms of voltage, which is fed into the comparator 22 is a function of the peak of the derivative. This is an important aspect of the circuit. When a QRS complex is found, the sample and hold circuit 26 is energized and it samples the peak of the QRS complex. The peak detector is then reset to a lower value ready to look for a new peak. When the peak is sampled, this sample voltage is fed through a buffer 27 which sets the reference voltage to about 44% of the peak value of a valid QRS complex. If no QRS complex is found for a certain length of time, an automatic update circuit 28 is energized to cause the automatic reference circuit which includes blocks 25, 26 and 27 to set a minimum voltage level.

Figure 2:
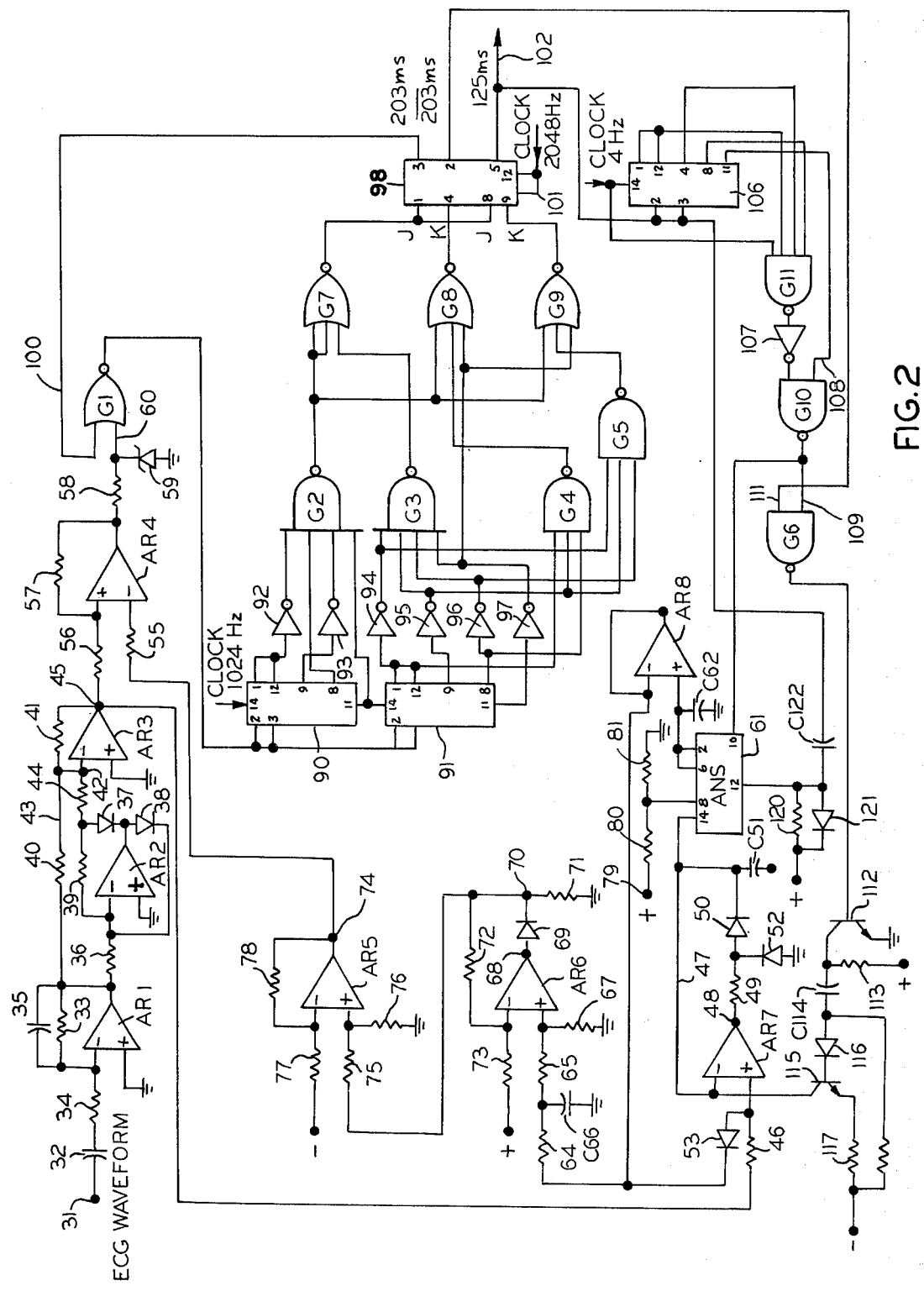
FIG. 2 is a more detailed circuit diagram of the device shown in FIG. 1.

Attention is now invited to FIG. 2 which shows the device depicted in FIG. 1 in greater detail.

In FIG. 2, the ECG waveform is supplied to the input terminal 31 of derivative circuit 20 which includes an operational amplifier AR1 connected as a differentiator. A capacitor 32 and a resistor 33 in a feedback circuit do the differentiating. A low valued input resistor 34 and a small capacitor 35 are used to minimize the response of the amplifier to noise, particularly noise with high frequency components.

The absolute value circuit includes operational amplifiers AR2 and AR3. AR3 is a unity gain amplifier and is used to invert the negative portions of the differential waveform. AR2 is involved in handling the positive signals which will be described first.

Positive signals from differentiator AR1 are supplied to the inverting terminal of AR2 through an input resistor 36. The output terminal of AR2 connects with the intermediate point of two diodes 37 and 38. Diode 38 is in a feedback circuit to the inverting terminal of AR2. The positive input signals to the inverting terminal of AR2 appear as negative signals on the output terminal of this amplifier. These negative output signals cause diode 37 to conduct. On the other hand, when negative portions of the differentiated signal are fed to the inverting terminal of AR2, the output signal from that amplifier is positive and diode 37 does not conduct.

Negative portions of the differentiated signals from AR1 go through a resistor 40 to the inverting terminal of AR3 and appear on its output terminal as positive signals. AR3 has a feedback resistor 41 which has the same value as resistor 40, thus giving AR3 unity gain for negative signals. The inverting terminal of AR3 serves as a summing junction 42. The signal at the anode of diode 37 is equal and opposite to the signal on line 43 for positive signals. The ratio of resistor 41 to 44 is two to one. The summing junction thus causes a gain of two for the signal at the anode of diode 37 and a gain of one for the signal on line 43 which results in a gain of one for the signal on the anode. Thus, the output signal of AR3 is unity and is always positive. This signal has substantially the shape shown in part 3C of FIG. 3.

From the output terminal 45 of AR3 the positive absolute value signal is fed to the noninverting terminal of an operational amplifier AR7 through an input resistor 46. AR7 is the positive peak detector of the absolute value of the differentiated waveform and has a substantially zero impedance feedback line 47 which makes it a substantially unity gain amplifier. Positive output signals from the output terminal 48 of AR7 are supplied to a resistor 49 and a diode 50 to a peak detector capacitor C51 which has one side connected to the negative supply. When there is a positive input to the noninverting terminal of AR7, capacitor C51 charges to peak value. When C51 reaches the peak of the input signal it can no longer charge through forward biased diode 50 but it cannot discharge because of the reverse biased diode 50. C51 charges to the highest positive peak of whatever waveform is differentiated. Since diode 50 is in the feedback loop of AR7, it introduces no voltage drop on the input signal.

Now to be described is the manner in which the reference voltage is developed which, if exceeded, fulfills one criteria for the differentiated waveform being considered an R-wave candidate. As mentioned earlier, the other criteria is that the reference voltage magnitude must be exceeded for about 11 milliseconds in this example before the circuitry makes a final decision that the differentiated signal represent an R-wave.

The absolute value of the differentiated waveform depicted in part 3B of FIG. 3 is compared with the reference voltage in a comparator AR4 The reference voltage, whose generation will be described soon, is supplied to the inverting terminal of AR4 through an input resistor 55. The absolute value of the differentiated waveform is supplied simultaneously to the noninverting terminal of AR4 through an input resistor 56 and a feedback resistor 57. When the reference voltage applied to the inverting input of AR4 is exceeded by the absolute value of the differentiated signal applied to the noninverting input, the output of AR4 goes high. This high signal is fed to one input 60 of a NOR gate G1. A resistor 58 and a zener diode 59 limit the input voltage to the one terminal of G1 to about 5 volts for compatibility with other logic elements in this example. When the input terminal 60 of G1 goes high the output of G1 will go low and this causes a counting or timing cycle to be initiated as will be explained in more detail later. It is sufficient to know at this time that the first interval counted in this embodiment is the approximate 11 millisecond interval during which the output of AR4 must be high to fulfill the time criteria for the existence of an R-wave. In a commercial design the interval is actually about 11.5 milliseconds which results from a whole number of counts at the particular clock rate used. The minimum permissible interval is probably about 6 milliseconds and the maximum about 20 milliseconds.

If the output of comparator AR4 switches high and drops back low before about 11 milliseconds has expired, it would be an indication that a true R-wave has not been detected for reasons which will be explained later.

The circuit for developing and automatically updating the reference voltage for comparator AR4 will now be described in detail. The detected peak voltage on C51 is supplied to pin 14 of an analog switch (ANS) 61 which may be a type DGM111. On a proper command, such as when an R-wave has been detected and 125 milliseconds has been timed out by another part of the circuitry to be described, the ANS 61 will switch and take a sample of the peak voltage on C51 and hold it on a sample and hold capacitor C62. Such sample is only taken when an R-wave is detected. The sampled voltage held on C62 is applied to the noninverting input of operational amplifier AR8 which is connected as a follower. The output of AR8 is supplied to the noninverting input of an operational amplifier AR6 through a filter circuit including resistors 64, 65 and capacitor C66. The filter smooths out the input voltage for the equivalent of about 3 or 4 heartbeats so that no instant change in the input of AR6 nor its output is obtained if a noise spike gets into the system or if the differentiated QRS complex would have changed suddenly due to a premature ventricular contraction, for example. It is undesirable for the reference voltage to change quickly by a great amount. Resistor 67 which connects to the noninverting terminal of AR6 may be considered a feedback resistor and its ratio in respect to resistor 65 is such that the output of AR6 will be established at preferably about 43 or 44% of the peak of the derivative voltage value in this embodiment but a percentage between 20 and 60% may be employed in some cases. Thus, the output terminal 68 of AR6 always has about 43 or 44% of the peak voltage which exists on the output of AR8.

When the circuit is first energized, the reference voltage is undetermined so it is necessary to set it at some definite value. As will be explained, the circuitry is such that if an R-wave is not detected for four seconds the sample and hold capacitor C62 is set to a predetermined d-c level. This is done by commanding ANS 61 to switch and apply a voltage of about 1 volt, in this example, to sample and hole C62 from a divider circuit, comprised of resistors 80 and 81 which are grounded at one end and connected to a power supply terminal 79.

AR6 also establishes a minimum voltage which the automatic reference, to be described, will drive down to and stop. The reason for setting a minimum is that if the R-wave becomes very small it is hard to distinguish it from noise so the reference should not go down so far that noise becomes a factor. The minimum voltage is established as follows: The output signal from AR6, as long as it is positive, will forward bias diode 69 and cause a positive voltage to appear on the junction 70 on top of a grounded resistor 71. Junction 70 cannot go negative and stays at zero regardless of how low the noninverting input of AR6 goes. However, normally when the input signal AR6 is adequate, 43% of this voltage will appear on point 70. An operational amplifier AR5 assures that the output voltage on its output terminal 74 and, hence, the reference voltage applied to the inverting terminal of comparator AR4 will not go below this predetermined value. For instance, if the output of AR6 at point 70 goes to zero, 0 volts will be applied to the noninverting input of AR5 which has an input resistor 75 and a grounded resistor 76 connected to it. AR5 also has a feedback circuit including a high value resistor 77 and a relatively low value resistor 78. The ratio of these resistors is such that the voltage appearing at output terminal 74 of AR5 can never go below 0.5 volts minimum in this example. Of course, the reference voltage on output terminal 74 of AR5 is normally higher if the peak voltage represented by the R-wave derivative is higher. There is a need for this minimum reference voltage for if it went too low the comparator AR4 would be triggered by noise or any transient in the system and it would sample all signals for their possibility of being an R-wave. It should be recognized, however, that the output of comparator AR4 may go high upon occurrence of a short duration noise spike under 11 milliseconds but this merely starts the counting period which is reset to zero if the noise signal disappears before 11 milliseconds which would be indicative of an R-wave. Thus, it is evident that comparator AR4 output must exceed the reference voltage magnitude for a predetermined amount of time before the presence of an R-wave is certain.

As mentioned earlier, NOR gate G1 responds to comparator AR4 tripping as a result of the absolute value of the derivative which is fed to its noninverting terminal exceeding the reference voltage on its inverting terminal. NOR gate G1 has to do with measuring and controlling the 11 millisecond period and other periods which are pertinent to operation.

Initiation of the timing periods will now be described. The output of NOR gate G1 is normally high. When it goes low as a result of one of its inputs going high due to the proper waveform magnitude or first criteria of R-wave detection being met, the low signal is applied to pins 2 and 3, respectively of a pair of counters 90 and 91. These may be type 7493 integrated circuit counters. A 1024 Hz clock pulse signal is applied to pin 14 of counter 90. The counters cooperate with a group of inverters 92-97, NAND gates G2-G5, NOR gates G7-G9 and a dual JK flip-flop 98 to produce some timing signals as will be explained.

Consider first how a pulse is produced at the end of an 11 millisecond interval if the derivative of the R-wave signal maintains a value above the reference level for the 11 millisecond interval. When the output of NOR gate G1 goes low in response to the ECG signal exceeding the reference voltage, this low signal is applied to pins 2 and 3 of counters 90 and 91 to start counting. When a number of clock pulses is counted equivalent to about 11.5 milliseconds, pins 1, 12 and 9 of counter 90 go low so that the outputs of inverters 92 and 93 go high. At the same time, pins 8 and 11 of counter 90 go high. Thus, at the end of about 11 milliseconds, all inputs to NAND gate G2 are high and its output will be low. Similarly, at the end of the 11 millisecond interval, all of the outputs from pins 1, 8, 9, 11, and 12 of counter 91 will be zero and, because of inversion by the respective inverters 94-97, all inputs to NAND gate G3 will be high and its output will be low. These two simultaneous low outputs of G2 and G3 are inputs to NOR gate G7 which is inverting so its output goes high. This high signal is applied to the J terminals or pin 1 and pin 8 of JK flip-flop 98, causing pin 3 and pin 5 to go high. When pin 3 goes high, this signal is applied to the other input 100 of Nor gate G1 which causes its output to continue low and thereby continues counting by the counters 90 and 91 after expiration of the 11 millisecond interval which has verified that a true R-wave has been detected. If the differentiated input signal to comparator AR4 would not have been maintained above the reference voltage input thereto for 11 milliseconds, it would have been indicative of no R-wave and counters 90 and 91 would have been reset to zero as a result of the output of G1 going high. The JK flip-flop 98 may be an integrated circuit type 74107. As indicated, adjacent its clock input terminal 101, this flip-flop is supplied with a 2048 Hz input clock signal which gates it.

Since the counters 90 and 91 continue counting when an R-wave is indicated by expiration of the 11 millisecond counting interval, the counters will continue to count for about 203 milliseconds in this example. This 203 millisecond interval is long enough to assure that a QRS complex has been completed but there would be reasonable certainty after about 140 milliseconds. At such time, the outputs of NAND gates G2 and G4 will go low and the output of NOR gate G8 will go high. This high signal is applied to the K terminal or pin 4 of JK flip-flop 98 which causes its pin 3 to go low. The low signal is applied to input 100 of NOR gate G1 which causes its output to go high, thus resetting counters 90 and 91 to zero.

When counters 90 and 91 have been energized for such length of time as to count 125 milliseconds equivalent, the inputs to a NOR gate G9 are such that its output will be high. This high output is applied to the K terminal or pin 11 of dual JK flip-flop 98 and this causes pin 5 of the flip-flop to go low at the end of 125 milliseconds. This 125 millisecond pulse appears on pin 5 and line 102 which may supply some R-wave detection indicating means, not shown. The pulse is also used for other purposes.

Pin 5 of JK flip-flop 98 is high for 125 milliseconds after counting begins. As indicated, when the output of this pin goes low at the end of 125 milliseconds it is used to operate an R-wave indicator. This change of state at the end of 125 milliseconds is used to reset the automatic update circuit of the detector. For this purpose a divide by N counter 106 is provided. This may also by a type 7493 integrated circuit counter. Its pin 14 is provided with a 4 Hz clock signal. Counter 106 is turned on at the end of 125 milliseconds by applying the low signal to its pins 2 and 3. If for some reason an R-wave is not detected, counter 106 and the logic of NAND gates G11 and G10 in conjunction with G6 provide about 4 seconds delay after the last 125 millisecond period has elapsed. If 4 seconds elapse, G11, G10 and G6 are enabled to produce a pulse. This results from the fact that after 4 seconds all of the inputs to NAND gate G11 are high and its output is low but inverted again by inverter 107 so the signal to one input of G10 is high. The other input 108 of G10 is also high as a result of it being connected to pin 11 of counter 106 which is also high. The two high inputs of G10 cause its output to go low. This low signal is applied to pin 10 of ANS 61 which causes it to switch and results in applying to the sample and hold C62 the potential established by the midpoint of the voltage divider comprised of resistors 80 and 81. Thus, sample and hold C62 will have a predetermined minimum voltage on it which is reestablished at least every four seconds if an R-wave is not detected.

The voltage on peak detector capacitor C51 is also reset if an R-wave is not detected in 4 seconds. C51 is set to a d-c level which is slightly lower than the voltage that existed on it during the 4 second waiting period. It keeps resetting every four seconds or at least until the reference circuit has reached its chosen minimum d-c level of 0.5 volts on output terminal 74 of AR5.

At the end of 203 milliseconds, pin 2 of JK flip-flop 98 goes high. This high signal is applied to one input 111 of G6 NAND gate. The other input of G6 is high since the QRS complex is still being detected and the output of G6 now goes low. This low output signal is applied to the base of a transistor 112 in the peak detector resetting circuit. The peak detector capacitor C51 is reset to a little lower d-c level such that the next peak will drive it back up to where it was originally or where it will seek a new peak. Transistor 112 has a collector resistor 113 and a coupling capacitor 114 which applies a positive pulse to another transistor 115 through a diode 116, thus turning transistor 115 on when transistor 112 is off. The collector of transistor 115 connects to the positive side of peak detector capacitor C51. The value of the emitter resistor 117 associated with transistor 115 is such that only sufficient current will drain off of C51 during the resetting pulse to reset its voltage at only about 0.5 volts lower than it was. Thus, after every R-wave is detected, there is resetting of the peak capacitor C51 after the sample and hold circuit has taken effect, that is, after 125 milliseconds so C51 will be able to charge to the next highest peak. When pin 5 of JK flip-flop 98 goes low, then C122 and R120 form a derivative circuit function which produces a negative pulse or spike which is applied to pin 12 or internally to pins 14 and 2 of ANS 61 which turns it on to put the peak voltage of C51 onto the sample and hold C62.

In summary, an R-wave detector has been described which produces output pulses or state changes on a line 102 indicative of each R-wave that has been detected. The reference circuit operates automatically to establish a reference voltage which is about 43% of the peak voltage detected from the R-wave derivative. The QR and RS segments of the QRS complex have a substantially constant slope so their derivatives are constant. The patient's ECG signal is compared to a reference value normally of about 43% of the peak of these voltages and the automatic resetting feature maintains this relationship. Noise signals do not affect detection adversely because they do not fulfill the time criteria for R-wave detection. Other components of the ECG waveform, such as the P and T waves, do not affect detection because they fulfill neither the time nor magnitude criteria. Thus, the detector is responsive to the R-wave only.

Figure 4:
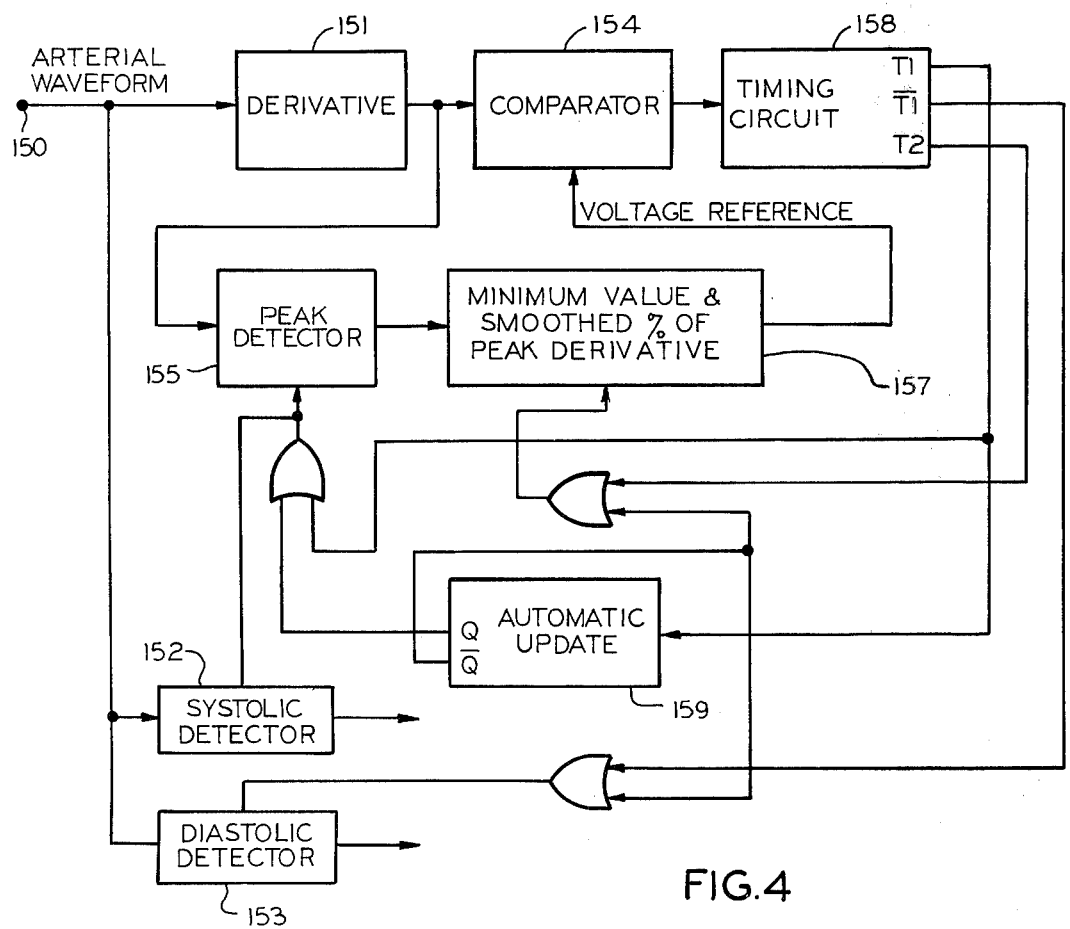
FIG. 4 is a block diagram of a blood pressure detector using the principles of the invention.

Attention is now invited to the FIG. 4 block diagram of a device for measuring systolic and diastolic blood pressure by means of a systolic upslope detector that employs the principles of the invention which are determining slope magnitude and duration of the systolic waveform upslope to distinguish it from other signals. In FIG. 4, the input arterial blood pressure waveform, such as depicted in part 6A of FIG. 6, is fed into three circuits from an input terminal 150 which obtains its waveform signal from a blood pressure sensor, not shown. The first of the three circuits is a derivative circuit 151 which is used to detect the upslope of the arterial waveform. The second circuit into which the waveform is fed is the systolic pressure detector 152 which is used to detect the peak pressure point. The third circuit is the diastolic detector 153 which is used to detect the minimum or valley pressure point. When the arterial blood pressure waveform signal is differentiated it is compared with a reference voltage in a comparator 154. This reference voltage is a function of the peak of the derivative of the pressure waveform; that is, when the systolic upslope is identified, the output of the peak detector 155 is fed into a buffer circuit represented by block 157 where the signal is reduced to about 50% of the peak value and smoothed. The output of the buffer 157 is the reference voltage which is supplied to the comparator 154.

When the comparator 154 switches to a high output state as a result of the differentiated signal input being greater than the reference voltage, counters in the timing circuit 158 begin to count and if the comparator remains tripped for a specified period of time that is indicative of a systolic upslope, it is accepted as a systolic upslope (SUS). If the comparator trips back before the time limit set for the counters, the counters will be cleared and the circuit will be ready to respond to the next upslope candidate which may trip the comparator 154.

When an SUS is found, timing pulses are suplied to the reference voltage circuit, an automatic updating circuit 159 and the systolic and diastolic detectors 152 and 153, respectively. If no SUS is found for more than 4 seconds, the automatic update circuit 159 generates pulses to reduce the reference voltage until an SUS is found or to a minimum level to keep from picking up noise, and the pulses also act on the systolic and diastolic detectors 152 and 153 so they will begin seeking new pressure levels.

A typical blood pressure waveform to be processed in the system just outlined is shown in part 6A of FIG. 6 and the signal resulting from differentiating this waveform is depicted in part 6B of FIG. 6. A more detailed circuit diagram of the device will now be described in reference to FIG. 5A primarily.

Figure 5A:
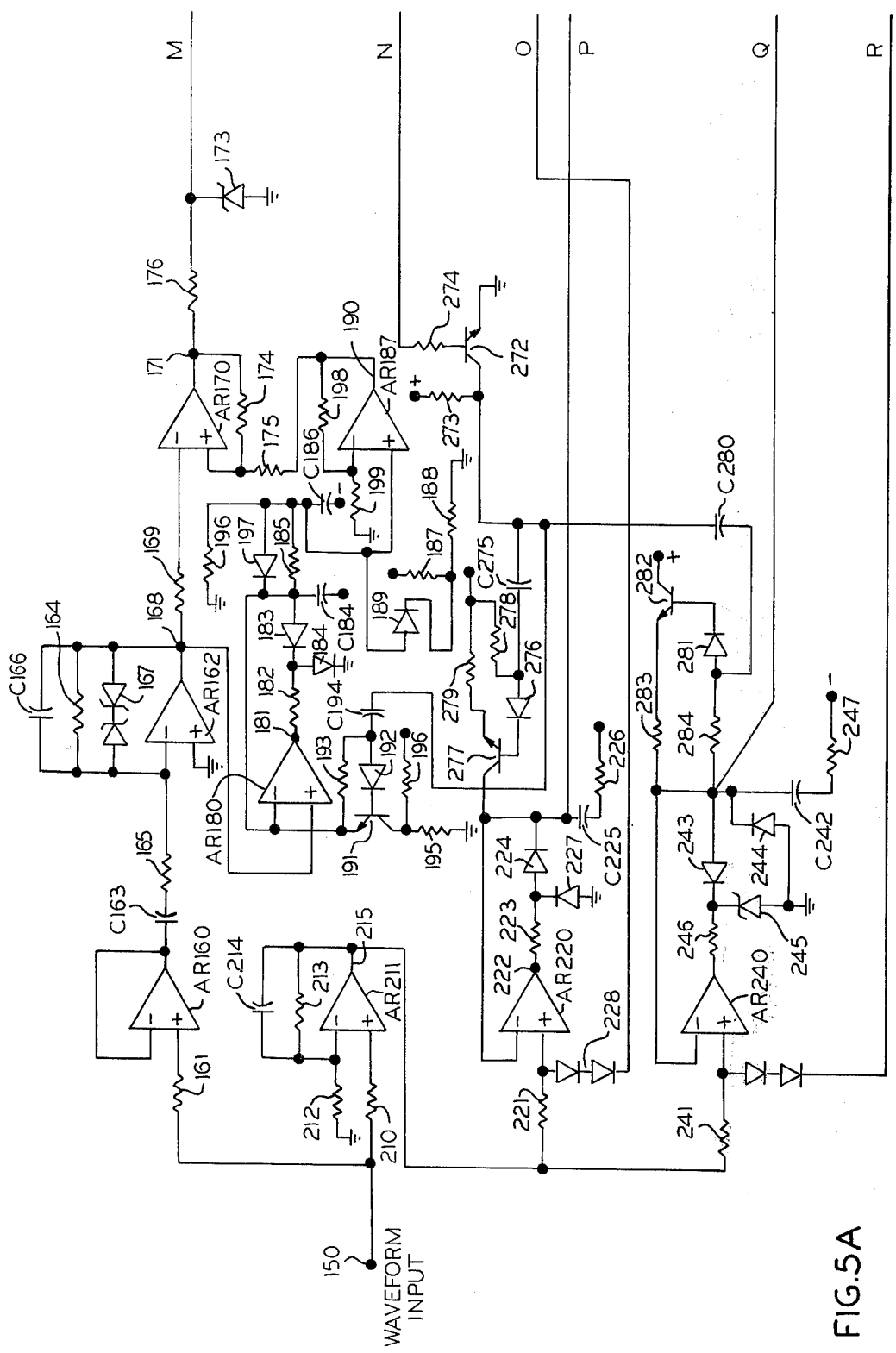
FIGS. 5A and 5B, connected by lines M to R, represent a more detailed circuit diagram of the device depicted in FIG. 4.

In FIG. 5A the input terminal 150 receives a waveform signal which corresponds with blood pressure and is generally similar to the waveform in part 6A of FIG. 6 which is produced by a blood pressure sensor, not shown, applied to the patient. The manner in which the signal is differentiated will be considered first. The waveform signal is applied to the noninverting terminal of a unity gain operational amplifier AR160 through an input resistor 161. The purpose of AR160 is to match impedances. The output signal or blood pressure representative waveform and any other signal from AR160 is fed to the inverting terminal of a differentiating operational amplifier AR162 which has a differentiating capacitor 163 and a differentiating resistor 164. High frequency noise is suppressed by coaction of a resistor 165 and a capacitor C166. A pair of zener diodes 167 set positive and negative limits on the output voltage of AR162. The differentiated signal appearing on the output terminal 168 of AR162 has the general shape of part 6B in FIG. 6 where it will be noted that the negative differential is taken and it is the negative peak of the derivative which is of value in the operation of the circuit as will be explained. The output signal from AR162 is supplied through an input resistor 169 to the inverting terminal of a comparator AR170. The noninverting terminal of AR170 receives a reference voltage which is developed in a manner which will be described hereinafter. For present purposes it is sufficient to know that when the derivative signal applied to the inverting terminal of comparator AR170 exceeds the reference voltage applied to the noninverting terminal, the comparator AR170 will trip which means that its output terminal 171 voltage will go high and this voltage will be applied to one input 172 of a NOR gate G15 which will switch and initate a counting period as will be explained more fully later. A zener diode 173 limits the high level of the AP 170 output signal to that which is compatible with the logic elements in the circuit.

The system is based on the principle that the best way to distinguish the blood pressure signals from other signals is to detect some unique characterstic of the arterial pressure waveform. The characteristic deemed to be the best is the systolic upslope of the waveform which is marked 177 in part 6A of FIG. 6. It has a specific magnitude and time duration and its slope is always substantially the same or merely changes slowly. When the upslope is detected, it follows that the previous minimum point or valley 178 of the waveform represents diastolic pressure and the next suceeding peak 179 represents systolic pressure. In the present system, the existence of a differentiated signal voltage which exceeds the reference voltage for about 21 milliseconds is taken as a criteria for the existence of a true systolic upslope. This time interval may be in the range of 10 to 40 milliseconds but about 21 milliseconds is preferred. If the signal to the inverting terminal of the comparator AR170 from the differentiator persists for somewhat less than 21 milliseconds in this example, the counters, to be described, reset and the system searches for the next true systolic upslope.

As stated, when the apparent systolic upslope signal exceeds the reference voltage for about 21 milliseconds, a true systolic upslope is assumed. Thus, it is necessary to develop a reference voltage for comparison and it is also necessary to detect the minimum value of the waveform or its valley and its maximum value or peak to determine diastolic and systolic pressures, respectively. The reference voltage circuit will now be described.

In FIG. 5A, the negative differential from output terminal 168 of the differentiator AR 162 is fed to the noninverting input of an operational amplifier AR 180. the output 181 of AR 180 connects to a resistor 182 and a pair of diodes 183 and 184. When the negative differentiated signal to AR 180 goes negative enough, its output goes negative and diode 183 conducts and charges a minimum peak or valley detector capacitor C184 negatively. C 184 in conjunction with a resistor 185 and another capacitor C186 constitutes an averaging circuit for all the peak derivative signals.

A voltage divider comprised of resistors 187 and 188 along with a diode 189 establishes a minimum boltage on C186 such that when its voltage goes below the voltage difference between resistors 187 and 188 minus the diode 189 voltage drop, the divider will hold the input of AR 187 at that minimum value. The d-c voltage level on C186 is always negative. The voltage on C186 is fed to the noninverting terminal of an amplifier AR187 which has feedback resistors 198 and 199. The ratio of the value of resistor 198 to that of 199 and resistor 185 to that of 196 results in a gain of 0.5 so that the voltage on the terminal 190 of AR 187 is about 50% of the negative peak derivative on C184 and it is this voltage which is used as a reference for comparator AR 170 to compare with the differentiated waveform signal to determine if it has sufficient magnitude to be a candidate for a systolic upslope. The minimum peak or valley detection circuit just described also has a reset circuit comprised of a transistor 191, diode 192, resistor 193, C194 and voltage divider resistors 195 and 196. A reset signal which is coupled through C194 will be described later.

The manner in which the peak 179 of the blood pressure waveform in FIG. 6A is detected will now be described. The waveform, in terms of volts per millimeter of mercury, comes in on input terminal 150 in FIG. 5A. This signal is applied through a resistor 210 to the noninverting terminal of an amplifier AR211 which acts as a gain buffer. AR 211 has an input resistor 212, a feedback resistor 213 and a capacitor 214 for establishing some gain. A true waveform signal appears on the output terminal 215 of AR 211 and this is fed to a peak detector amplifier AR220 which has an input resistor 221 connecting to the amplifier's noninverting terminal.

Peak detector amplifier AR220 has connected to its output terminal 222 a resistor 223 which is in series with a diode 224 connected to a peak detector capacitor C225. C225 connects to a negative supply through a resistor 226. C225 charges to the peak voltage of the blood pressure waveform and is prevented from discharging to a lower value by diode 224 which is reversely nonconductive after the peak is reached.

About 200 milliseconds after a systolic upslope has been detected there is high degree of certainty that the peak has been passed since it is unlikely that the upslope would persist actually for more than 150 milliseconds in any patient. Thus, the peak voltage on C225 is sampled in about 200 milliseconds after the output of comparator AR170 goes high by means which will be described later. C225 connects to pin 14 of an analog switch ANS 229. When pin 12 of ANS 229 receives a trigger pulse at about 200 milliseconds after a systolic upslope has been detected, pin 14 is switched or connected to pin 2 which thereby connects C225 to a sample and hold capacitor C230. Thus, C230 has a voltage which is representative of the peak of the blood pressure waveform or, in other words, systolic pressure. The voltage on C230 is supplied to the noninverting terminal of a unity gain operational amplifier AR231 on whose output terminal 232 systolic blood pressure, in terms of millivolts per millimeter of mercury appears. This signal may be fed to a systolic blood pressure indicator, not shown, by way of a line 233.

The valley point 178 or diastolic pressure of the blood pressure waveform in part 6A of FIG. 6 is also detected. This is done in FIG. 5A with an amplifier AR 240 and its associated circuitry. The blood pressure waveform from AR211 is fed to the noninverting terminal of AR240 through a resistor 241. The negative peak or valley 178 drives the output of AR240 negatively and this valley voltage appears on a capacitor C242. This valley voltage is held on C242 by the diodes 243 and 244. C242 is connected with pin 8 of ANS 229. By means which will be explained after the valley or threshold of a systolic upslope has been detected, the voltage on C242 is transferred to a valley voltage sample and hold capacitor C248. This is done, as will be explained by applying a trigger signal to pin 10 of analog switch ANS 229 in which case pins 8 and 6 thereof are connected together and C248 is charged.

The voltage on C248 which is representative of the most negative peak 178 of the blood pressure waveform is applied to the noninverting terminal of a unity gain amplifier AR249 whose output terminal 250 has an average voltage on it representative of diastolic blood pressure in terms of millivolts per millimeter of mercury. This diastolic pressure signal may be sent to a suitable indicating meter, not shown, by way of line 251.

Consideration will now be given to the various timing and reset features of the circuit. Recall that two criteria must be met before the detected differentiated waveform signal is considered a systolic upslope signal. These criteria are the duration of the upslope and its magnitude. As mentioned earlier, the magnitude of the differentiated waveform is compared with a reference voltage in comparator AR 170. If this reference voltage is exceeded for about 21 milliseconds, it is evidence that a systolic upslope has occurred and has been detected. The manner in which this and other time intervals for indicating and resetting are measured will now be described.

The timing circuit includes two integrated circuit counters 260 and 261 which may be type 7493. Counters 260 and 261 are enabled when the peak negative differential input signal exceeds the reference voltage on comparator AR170. As explained earlier, when the output of comparaator AR170 goes high, this signal is applied to an input 172 of NOR gate G15, causing its normally high output to go low. The low output signal is applied to pins 2 and 3 of counters 260 and 261, thus turning them on and initiating a counting period. Counter 260 will count for 21 milliseconds provided the differentiated signal peak exceeds the reference voltage for that period of time which is indicative of a systolic upslope being detected. If the reference voltage is not exceeded for that period, the counters 260 and 261 will reset when the output of comparator AR170 drops back low. If the counter reaches the 21 millisecond time period, the other input 262 of NOR gate G15 will go high and counting will continue for another 200 milliseconds or so when there is certainty that a waveform peak has been reached.

Counter 260 is provided with a 1024 Hz clock frequency through inverter 263. When counter 260 is enabled, it will reach a count which is equivalent to about 21 milliseconds at which time NAND gates G17 and G18 will both have all high inputs in which case their outputs will both be zero or low. The low signals are applied to the inputs of a NOR gate G22 whose output will then go high. This high output signal is applied to pin 1 of a dual JK flip-flop 264 which may be type 74107. Those skilled in the art will be able to trace the signal from counter 260 through the various inverters 265-270 and determine how the output of G22 may go high when a count equivalent to 21 milliseconds is reached. In any event, when pin 1 of JK flip-flop 264 goes high its output pin 2 goes low and this signal is applied to one of the inputs of a NAND gate G26 which, of course, is normally high. Application of the low signal, causes the output of G26 to go high and this high signal is applied to input 262 of NOR gate G15 whose output then will continue to remain low to thereby sustain counting by counter 260 for about 200 milliseconds even though the signal may have disappeared from the other input 172 of G15 because of the upslope having peaked in much less time.

At about 200 milliseconds, the inputs to NOR gate G23 are low and its output which is applied to pin 4 of the JK flip-flop 264 is high. This causes pin 2 of flip-flop 264 to go high again at the end of 200 milliseconds. The output of G23 also goes to pin 8 of TK flip-flop 264 to begin the 15 milliseconds time out after the end of the 200 millisecond period. The counting status is such that the output of NOR gate G24 goes high and pin 11 of JK flip-flop 264 therefore goes high. Pin 11 is the K input to JK flip-flop 264 and when it goes high, its complement output pin 6 goes high. This happens about 15 milliseconds after expiration of the 200 millisecond period. When pin 5Q output goes high, the high signal is transferred by way of a line 251 to an input of a NOR gate G30 which goes high so its output goes low. This signal is transferred through an inverter 271 which enters the resetting circuit for the peak and valley detector amplifiers AR220. and AR240. The peak detector AR220 is reset by applying this resetting signal to the base of a transistor switch 272 having a collector resistor 273 and a base resistor 274. The collector connects to a capacitor C275 which couples the resetting signal through a diode 276 to the base of a transistor 277 which has base and emitter resistors 278 and 279, respectively. When resetting transistor 277 is caused to conduct, the voltage on peak detector capacitor C225 is dropped slightly so that it can respond to the next ensuing peak if it is somewhat lower than the previous one.

Similarly, the valley detector AR240 is reset when the output of G30 NOR gate goes low. When transistor 272 conducts in response to the resetting signal, the signal is also coupled through a capacitor C280 through a diode 281 to the base of a transistor 282 whose collector is connected to the positive supply. The conduction interval is such that the output of valley detector amplifier AR240 goes more positive and charges capacitor C242 slightly more positive so that it can seek the next ensuing valley. Transistor 282 has an emitter resistor 283 and a base resistor 284, the latter of which sets the time constant of the discharge such that the voltage on C242 is not raised excessively.

Attention is now invited to the automatic update circuit which constantly causes the systolic and diastolic pressures to be sampled at a 2 Hz or twice per second rate to quick step them for finding a new valley and a new peak if the systolic upslope should be lost. In such case the existing d-c levels should be found as quickly as possible.

Figure 5B:
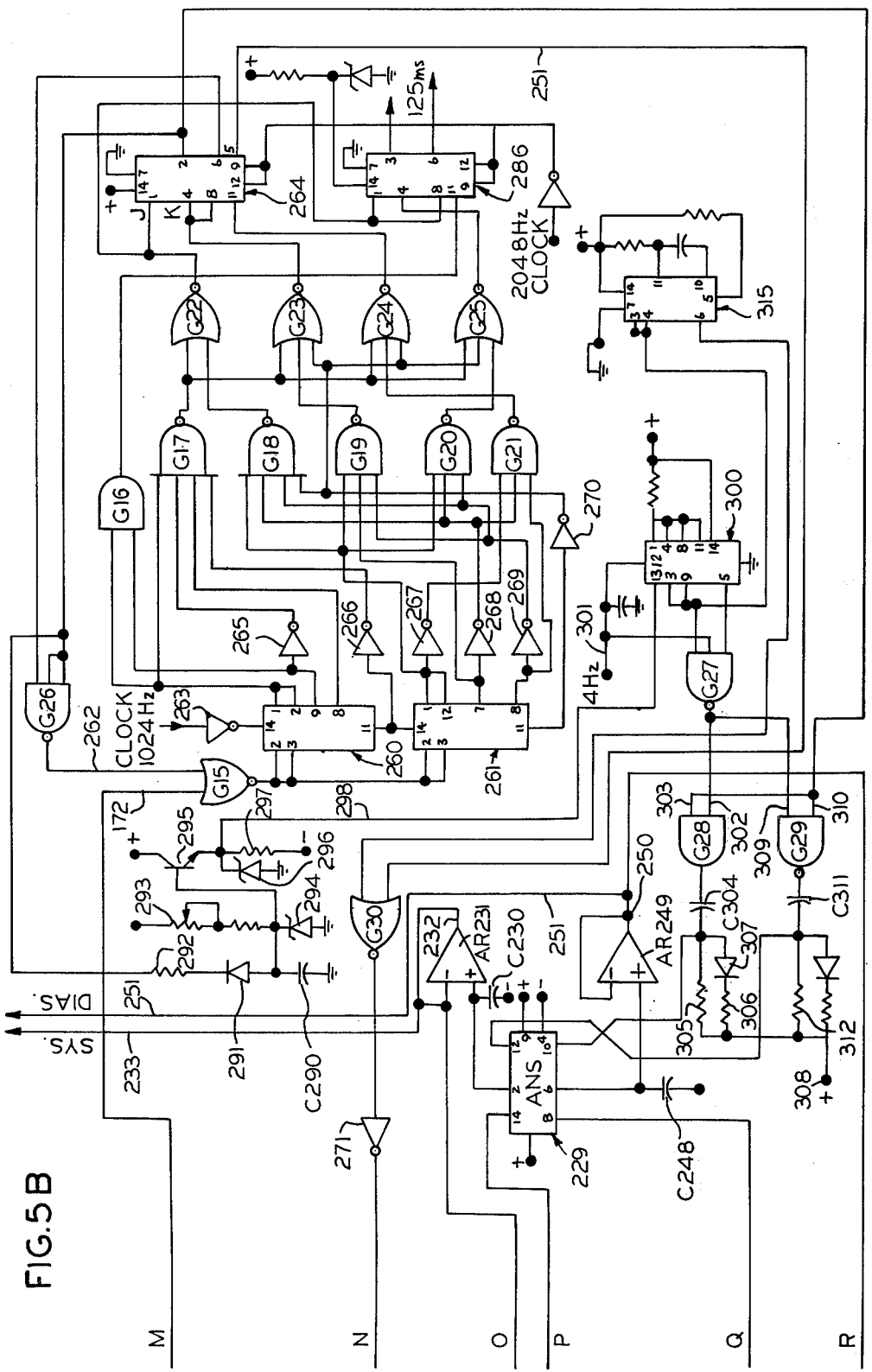

The automatic update circuit comprises a capacitor C290 which is located near the top and center of FIG. 5B. C290 is charged from positive supply through an adjustable resistor circuit 293 which is limited by a zener diode 294. As long as there is a high going low pulsating signal available from pin 2 of JK flip-flop 264, C290 does not charge. If the signal from pin 2 of JK flip-flop 264 remains high, C290 has a chance to charge up, at a charge rate set by resistor 293. Resistor 293 is adjusted such that after 3½ seconds the charge on C290 is high enough to allow line 298 to be at a level to trigger pin 13 and turn on JK flip-flop 300 which is here used as a simple counter. This is done, of course, by tying the J and K inputs 1, 4, 8 and 11 together. Flip-flop 300 is provided with a 4 Hz clock input 301. At the end of the 3½ second period, when a trigger pulse is applied to pin 13 of flip-flop 300, it will produce pulses on its pins 3, 5 and 9. The pulses are applied to the inputs of a NAND gate G27. The output of G27 is low when all of its inputs are high. this low pulse is applied to one input 302 of an AND gate G28. The other input 303 to AND gate G28 is connected back to pin 2 on JK flip-flop 264 which remains high when no systolic upslope is found. The low input 302 to AND gate G28 results in its output being low or negative. This low signal is coupled through a derivative circuit including a capacitor C304 and a resistor 305. The other junction of the resistor 305 is tied to positive supply 308 which has a voltage level compatible with digital logic such as five volts. The negative differentiating pulse through C304 is applied to pin 10 of analog switch ANS 229 which causes pins 6 and 8 thereof to be effectively connected in which case charge from valley detector capacitor C242 is transferred to sample and hold capacitor C248 to thereby update diastolic pressure if the arterial pulse is missing for about 3½ seconds.

Secondly, systolic pressure is automatically sampled and updated. When the sampling pulse coming from the output of NAND gate G27 returns to low, thus causing the input 309 to a NAND gate G29 to be low, and since there is no systolic upslope being detected, input 310 of NAND gate G29 is high causing its output to go high due to inversion. When input 309 to G29 switches high the output of G29 goes low and it is coupled through a derivative circuit including capacitor C311 and a resistor 312. The pulse is applied to pin 12 of analog switch ANS 229 which, when it goes low, causes conduction between pins 14 and 2 thereof in which case sample and hold capacitor C230 begins to charge to the level of peak detection capacitor C225. In this manner, diastolic pressure is updated first whenever something happens to lose pulse pressure for 3½ seconds and systolic pressure is updated secondly.

As mentioned earlier, resetting of the peak and valley detectors AR 220 and AR240 is done about 15 milliseconds after the 200 millisecond count period has terminated. A one-shot multivibrator 315 is involved. Each time a 4 Hz pulse comes into counter 300 and a 2 Hz pulse comes along, its pin 3 and pin 9 go low and the one-shot multivibrator 315 is triggered by way of its pin 4. When the one-shot 315 is triggered there is an output on its pin 6 which goes high for 15 milliseconds. This signal is coupled to NOR gate G30 and since the other input to G30 is low at this time, its output goes low. Then, as explained earlier, it goes through inverter 271 which then has a high output. After 15 milliseconds has elapsed, the output of inverter 271 goes low again. Up to this time the collector of transistor 272 is low and it goes high and effects resetting of the peak and valley detectors as explained earlier.

At the right side of FIG. 5B there is a JK flip-flop marked 286 which is used for supplying a rate indicating meter, not shown. It has an output on its pin 3 at the end of the 125 millisecond count interval which drives the rate indicator. Pin 6 of flip-flop 286 is a 2 millisecond output that is triggered at the same time as the 200 millisecond pulse is triggered on as a result of the tie with pin 1 of JK flip-flop 264. Pin 6 of 286 goes high when pin 8 of 286 goes high. When inputs to NOR gate G25 go low, its output goes high and cause pin 4 of flip-flop 286 to go high. Pin 4 is the K input which causes pin 3 of flip-flop 286 to reset to low.

Although an R-wave detector embodiment and a systolic upslope detector and a diastolic and systolic pressure indicating embodiment of the invention have been described in considerable detail, such description is intended to be illustrative rather than limiting since the principle of multi-criteria waveform identification can be applied to various physiological waveform detectors and the invention is to be limited only by construing the claims which follow.

We claim:
1. A device for detecting a waveform signal portion in the presence of other signals by using the characteristic time rate of change or slope of the waveform signal portion as criteria for its existence, comprising:

a. means for differentiating said waveform signal to produce a differentiated signal having a portion whose magnitude is representative of said slope criteria,
 b. means for detecting the peak magnitude of said differentiated signal,
 c. means for producing a reference signal including means for converting said peak magnitude signal to a signal representing a predetermined percentage thereof, said last named signal constituting said reference signal and corresponding in magnitude with the derivative of the slope of said waveform signal portion,
 d. comparator means having inputs for receiving said differentiated signal and reference signal, respectively, said comparator means producing an output signal change when said differentiated signal magnitude is greater than said reference signal,
 e. timing means responsive to occurrence of said last named output signal change by initiating measurement of a first time interval which, if completed, is indicative of said waveform portion meeting the time criteria, said timing means also being responsive to terminate measurement of said first interval if said output signal discontinues before expiration of said predetermined period,
 f. means responsive to completion of said first time interval by actuating said timing means to continue to measure a second time interval, and
 g. resetting means responsive to completion of said second interval by resetting said reference signal producing means to produce a reference signal having a different value than the preceding reference signal existing when said comparator produced the aforementioned output signal.

2. A device for detecting a particular waveform signal in the presence of other signals, comprising:
 a. means for differentiating said signals,
 b. means for detecting a peak value of said differentiated signal,
 c. means for sampling said detected peak value signal in response to a signal indicative of said particular waveform being detected,
 d. means for producing a reference signal from said sampled peak signal which said reference signal is a predetermined percentage of the sampled peak magnitude of said differentiated signal,
 e. means for continuously comparing said differentiated signal with said reference signal, said comparing means changing its output signal in response to said differentiated signal exceeding said reference signal as an indication of a magnitude characteristic of said particular waveform,
 f. timing means responsive to said output signal change by initiating measurement of a first predetermined time interval indicative of a time characteristic of said particular waveform, and
 g. output means responsive to said timing means reaching said predetermined interval by producing an output signal incidative of said particular waveform being detected.

3. A device for detecting the minimum and maximum magnitudes of a particular waveform signal in the presence of other signals by using plural characteristics of said waveform signal for identification thereof, comprising:
 a. means for receiving and differentiating said signals,
 b. means for producing a reference signal, c. means for comparing the magnitude of said differentiated signals with the magnitude of said reference signal, said comparing means changing its output signal in response to said differentiated signal magnitude being greater than said reference signal magnitude, said signal change being indicative of one characteristic of said waveform if said change is sustained for a predetermined time interval and being indicative of a waveform which it is not desired to detect if it is sustained for less than said predetermined time interval.

d. timing means for measuring the duration of said change, means for detecting said undifferentiated waveform signal, and f. means for sampling the minimum and maximum magnitudes of said last named detected signal in response to said timing means measuring a change duration at least as long as said predetermined interval, and means for storing said minimum and maximum signals.

4. A device for detecting a particular waveform signal in the presence of other signals, comprising:

a. means for receiving and producing differentiated signals whose time intervals correspond with the slopes of the signals wherein the slope of the waveform signal of interest is identified by it having a known first predetermined time interval, b. means for producing a reference signal which is representative of the magnitude of said derivative of said waveform signal;

c. means for sampling the peak of said differentiated signal in response to said particular waveform being detected, d. means responsive to said timing means timing a second interval by resetting said reference signal producing means to a new signal level, e. means for comparing said differentiated signals with said reference signal whereby if any differentiated signal is greater than said reference signal for said first predetermined time interval it is indicative of detecting said particular waveform signal of interest and if greater than said reference signal for other than said predetermined interval it is indicative of a signal which is not of interest, said comparing means producing an output signal when said differentiated signal is greater, and f. timing means for determining the intervals of said signals whereby to accept signals of interest and reject signals which are not of interest.

5. The device set forth in claim 4 wherein:

a. said means for producing a reference signal includes means for detecting the peak value of said differentiated signal, b. first storage means for storing said peak value, c. second storage means, d. switch means operable by selected signals to transfer said peak value to said second storage means, e. said means for producing said reference signal being controlled by the value in said second storage means to produce a reference signal which is a predetermined percent of said peak value.

f. said timing means being responsive to said differentiated signal exceeding said reference signal for a predetermined time by continuing timing and producing a first output signal and a later second output signal, g. said switch means responding to said first output signal by said transferring of said peak value from said first to said second storage means, said second output signal resetting said first storage means to enable said first storage means to store the ensuing detected peak value.

6. The device set forth in claim 5 including:

a. further timing means adapted to be reset to restart a substantial time interval upon occurence of each of said first output signals and to produce a further output signal at the end of said substantial timing interval if said further timing means is not reset, and b. means for producing a predetermined potential, said switch means being responsive to occurrence of said further output signal by applying said predetermined potential to said second storage means whereby to update the potential in said second storage means if said first output signal does not occur within said substantial time interval.

7. The device set forth in claim 5 including:

a. circuit means including switch means connected to said first storage means, said last named switch means being operated in response to occurrence of said second output signal from said timing means to update the signal in said first storage means.

* * * * *